(12) United States Patent
Juvan

(10) Patent No.: US 9,289,714 B1
(45) Date of Patent: Mar. 22, 2016

(54) DEVICE FOR ADSORBING THE HYDROGEN SULFIDE COMPONENT OF EXHAUSTED CALIBRATION GASES

(71) Applicant: JuvanCo Industries, LLC, Evanston, WY (US)

(72) Inventor: Matthew Cory Juvan, Evanston, WY (US)

( * ) Notice: Subject to any disclaimer, the term of this patent is extended or adjusted under 35 U.S.C. 154(b) by 0 days.

(21) Appl. No.: 14/516,881

(22) Filed: Oct. 17, 2014

(51) Int. Cl.
*B01D 53/02* (2006.01)
*B01D 53/04* (2006.01)
*G01N 33/00* (2006.01)
*B01D 46/00* (2006.01)

(52) U.S. Cl.
CPC ........ *B01D 53/0407* (2013.01); *B01D 46/0023* (2013.01); *G01N 33/0006* (2013.01); *B01D 2253/102* (2013.01); *B01D 2257/304* (2013.01)

(58) Field of Classification Search
CPC ........... B01D 53/1462; B01D 53/1468; B01D 2257/304
See application file for complete search history.

(56) References Cited

U.S. PATENT DOCUMENTS

| | | | |
|---|---|---|---|
| 3,974,256 A | 8/1976 | Wheelock et al. | |
| 4,002,720 A | 1/1977 | Wheelock et al. | |
| 4,061,476 A | 12/1977 | Holter et al. | |
| 4,561,976 A * | 12/1985 | Houser | C02F 1/288 210/290 |
| 4,831,208 A * | 5/1989 | Zarchy | C10G 25/00 208/120.3 |
| 4,983,365 A | 1/1991 | Denny et al. | |
| 5,125,935 A | 6/1992 | Nakaya et al. | |
| 5,177,050 A | 1/1993 | Schubert | |
| 5,360,468 A | 11/1994 | Schubert | |
| 5,407,466 A | 4/1995 | Lokhandwala et al. | |
| 5,869,009 A * | 2/1999 | Bellefeuille | B01D 53/04 422/171 |
| 6,284,545 B1 | 9/2001 | Warburton et al. | |
| 6,395,073 B1 * | 5/2002 | Dauber | B01D 39/1692 360/99.17 |
| 6,404,205 B1 | 6/2002 | Kitamura | |
| 6,740,141 B2 | 5/2004 | Espin et al. | |
| 6,858,192 B2 | 2/2005 | Graham et al. | |
| 6,863,713 B1 | 3/2005 | Ghosal et al. | |
| 7,014,689 B2 | 3/2006 | Lookeren et al. | |
| 7,101,417 B2 | 9/2006 | Graham | |
| 7,241,430 B2 | 7/2007 | Graham | |
| 7,651,597 B2 | 1/2010 | Saffell et al. | |
| 7,704,380 B2 | 4/2010 | Shibata et al. | |
| 8,551,229 B2 | 10/2013 | Hufton et al. | |
| 8,646,341 B2 * | 2/2014 | Schulten | G01N 1/2205 422/88 |
| 8,882,874 B1 * | 11/2014 | Cross | B01D 46/00 55/481 |
| 2004/0035183 A1 * | 2/2004 | O'Brien | G01N 1/2202 73/23.27 |
| 2009/0090240 A1 * | 4/2009 | Husain | B01D 53/84 95/1 |
| 2009/0230052 A1 * | 9/2009 | Hunsinger | B01D 53/02 210/498 |
| 2014/0011666 A1 * | 1/2014 | Yoshizaki | A23L 1/304 502/7 |
| 2015/0052864 A1 * | 2/2015 | Jackson | B01D 46/2411 55/486 |

* cited by examiner

*Primary Examiner* — Christopher P Jones
(74) *Attorney, Agent, or Firm* — Larry J. Guffey; Oliver & Grimsley, LLC

(57) ABSTRACT

A portable and disposable device for adsorbing the hydrogen sulfide component of the calibration gases that would otherwise be released into the atmosphere during the calibration of such a detector includes: (a) an activated carbon bed having a configuration adapted to allow for a specified flow rate of the calibration gas, (b) an upstream and a downstream hydrated, particulate filter, (c) an upstream and a downstream hydrophobic filter, (d) a conduit having a configuration adapted to enclose and assemble the activated carbon bed, hydrated, particulate filters and hydrophobic filters; and wherein the hydrophobic filters and hydrophobic filters each have a configuration that is adapted to maintain the humidity level in the activated carbon bed above a set level.

8 Claims, 1 Drawing Sheet

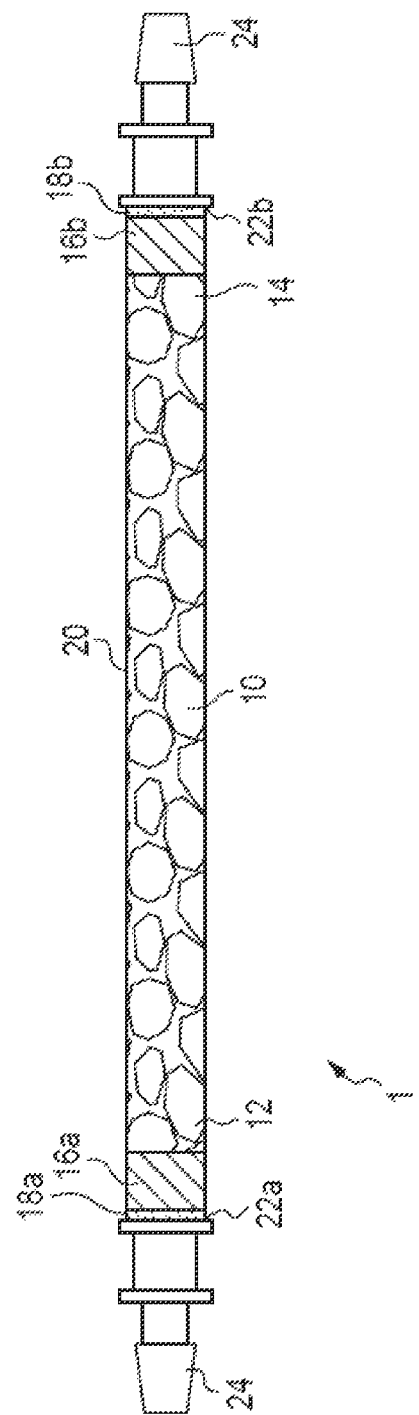

DEVICE FOR ADSORBING THE HYDROGEN SULFIDE COMPONENT OF EXHAUSTED CALIBRATION GASES

BACKGROUND OF THE INVENTION

1. Field of the Invention

The present invention generally relates to gas separation processes and analytical chemical testing equipment. More specifically, the invention is directed to devices and methods for adsorbing the hydrogen sulfide component of the calibration gases that would otherwise be released into the surrounding atmosphere during the calibration of portable gas detectors.

2. Description of the Related Art

Gas detectors and monitors are commonly used in a wide assortment of industrial applications. For example, they are used in the oil and gas industry, power plants, chemical plants, pig farms, grain elevators, sewer plants, landfills and many more places. In these industrial applications, gas detectors and monitors are generally used to monitor and detect the presence of hazardous and explosive gases and oxygen levels in the work environment.

Such gas detectors and monitors usually utilize a number of various types of sensors that are designed to detect and respond to specific, being-tested-for or targeted gases. This use of multiple sensors results in most of these detectors being able to monitor for any one of a number of common gases, the most common of which are oxygen, carbon monoxide, hydrogen sulfide and methane (i.e., the lower explosive limit (LEL) of methane). Single sensor monitors are typically used when there is the potential for exposure to a single gas. The sensors of most gas detectors require a test (i.e., a "bump" test) to confirm that the sensor or sensors are working properly before each use of the detector. Additionally, these sensors also need to be calibrated on a regular basis to make sure their output signals are within an expected or predicted range to known concentrations of the calibration gas. In both types of testing, the test or calibration gases are passed over the sensors and are eventually released into the surrounding or ambient environment. Typical calibration gases include among others: toxic hydrogen sulfide, $H_2S$, at 25 ppm or lower, non-toxic methane, $CH_4$, at 50% LEL (lower explosive limit) which is 2.5% (25,000 ppm) by volume methane, oxygen, $O_2$, concentration ranges from 12% to 18%, and toxic carbon monoxide, CO, at either 50 ppm or 100 ppm. These gases have a balance of air or nitrogen.

When the calibration gas being used is toxic, those who perform such "bump" and calibration tests have reported problems due to the levels of the toxic gases that are released into the surrounding or ambient environment during such tests when they cannot be performed in a ventilated area. Exposure problems when the calibration gas is hydrogen sulfide are often of specific concern.

Hydrogen sulfide is a known highly toxic and flammable gas that is heavier than air and often initially recognized as having a very pungent, rotten-egg-like smell at concentrations as low as 0.005 ppm. It is considered a broad-spectrum poison because it can poison several different systems in the body, although the nervous system is most affected. Its OSHA time-weighted, average exposure limit (TWA, an 8 hour time-weighted average) is 10 ppm. Short-term, exposure to low concentrations can result in eye irritation, a sore throat and cough, nausea, shortness of breath, and fluid in the lungs. Longer-term exposure to such concentrations may result in fatigue, loss of appetite, headaches, irritability, poor memory, and dizziness. Short-term, high-level exposure (i.e., >500 ppm) can induce immediate collapse, with loss of breathing and a high probability of death.

To avoid hydrogen sulfide exposure problems, what is needed is a better way to minimize the amount of this highly toxic gas that is released into the surrounding environment during such gas detector testing procedures.

A quick survey of the patent literature in this area reveals many processes for removing hydrogen sulfide from a gas stream. See, for example, U.S. Pat. Nos. 3,974,256, 4,002,720, 4,061,476, 4,983,365, 5,125,935, 5,177,050, 5,360,468, 5,407,466, 6,284,545, 6,404,205, 6,740,141, 6,858,192, 6,863,713, 7,014,689, 7,101,417, 7,241,430, 7,651,597, 7,704,380, 8,551,229, and 8,646,341. However, none of these are readily applicable for dealing with the small quantities of calibration gases that are utilized in the various gas detector, testing procedures. Thus, there is a continued need for new devices and new methods that can better and is more efficiently remove the hydrogen sulfide component of a calibration gas that would otherwise be released into the surrounding environment during the testing of gas detectors.

SUMMARY OF THE INVENTION

Recognizing the need for improved methods, devices and systems for removing the hydrogen sulfide component of a calibration gas that would otherwise be released into the surrounding environment during the testing of gas detectors, the present invention is generally directed to providing such improved methods, devices and systems.

In a preferred embodiment, the present invention is a portable device for adsorbing the hydrogen sulfide component of the calibration gases that would otherwise be released into the surrounding atmosphere during the calibration of a portable gas detector. This device includes: (a) an activated carbon bed having upstream and downstream ends and a configuration adapted to allow for a specified flow rate of the calibration gas from the downstream end to the upstream end of the activated carbon bed, (b) an upstream and a downstream hydrated, particulate filter, is the upstream particulate filter situated such that it is adjacent the upstream end of the activated carbon bed and the downstream particulate filter situated such that it is adjacent the downstream end of the activated carbon bed, (c) an upstream and a downstream hydrophobic filter, the upstream hydrophobic filter situated such that it is adjacent and upstream of the upstream hydrated, particulate filter and the downstream hydrophobic filter situated such that it is adjacent and downstream of the downstream hydrated, particulate filter, (d) a conduit having a configuration adapted to enclose and assemble the activated carbon bed, upstream and downstream hydrated, particulate filters and upstream and downstream hydrophobic filters and direct the flow of the calibration gas through the device at the specified flow rate; and wherein the hydrophobic filters and hydrophobic filters each have a configuration that is adapted to maintain the humidity level in the activated carbon bed above a set level so as to ensure a desired degree of adsorption of the hydrogen sulfide at the specified flow rate of the calibration gas.

Thus, there has been summarized above (rather broadly and understanding that there are other preferred embodiments which have not been summarized above) the present invention in order that the detailed description that follows may be better understood and appreciated.

BRIEF DESCRIPTION OF THE DRAWINGS

FIG. 1 is a schematic representation of a preferred embodiment of the present invention.

DESCRIPTION OF THE PREFERRED EMBODIMENT

Before explaining at least one embodiment of the present invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

The present invention generally relates to devices and systems for removing the hydrogen sulfide component of a calibration gas that would otherwise be released into the surrounding environment during the testing of a hand-held, portable gas detector. FIG. 1 provides a schematic illustration of a preferred embodiment of the present invention 1. Shown in FIG. 1 is a disposable device that includes an activated carbon bed 10 having upstream 12 and downstream 14 ends and a defined length therebetween and a centerline extending between the ends, and adapted to allow for a specified flow rate of the calibration gas through the length of the activated carbon bed. On its upstream and downstream ends is a hydrated, particulate filter 16a, 16b filter that has a configuration which includes a prescribed humidity level.

Upstream and a downstream of these filters 16a, 16b is a hydrophobic filter 18a, 18b. Both the hydrophobic filters and the hydrated, particulate filters have configurations that are adapted to maintain the humidity level in the activated carbon bed above a set level so as to ensure a desired degree of adsorption of the hydrogen sulfide at the specified flow rate of the calibration gas through the gas detector. A tubular conduit 20 has two ends 22a, 22b and a configuration adapted to allow it to enclose and assemble the activated carbon bed, the upstream and downstream hydrated, particulate filters and the upstream and downstream hydrophobic filters and to direct the flow of the calibration gas through this assemblage, while also enclosing the device such that it can be disposed of as standard trash, rather than as a hazardous material. Non chemically-reactive connectors 24 are connected to each of the conduit's ends and have configurations that are adapted to allow either end of this assemblage to be connected directly or indirectly to the exhaust port of the gas detector system from which the calibration gas is released.

The design of this preferred embodiment of the present invention and the various elements used in it were guided by the fact that activated carbon is known to be an excellent adsorbant of hydrogen sulfide at high humidity levels. However, most manufactures of calibration and test gases go to considerable efforts to make sure their gases are as dry as possible in order to avoid creating moisture-related problems within gas detectors and monitors and their calibration and testing equipment.

In a preferred embodiment, the present invention has been configured such that it can adsorb the quantity of hydrogen sulfide that is contained in a standard size (e.g., 58 liter) bottle of a calibration gas which contains 25 ppm hydrogen sulfide and flows though a gas detector at a flow rate of approximately 0.5 liters per minute. For this preferred embodiment operating at such a flow rate, the present invention utilized circular, 1.0 cm diameter, PVC tubing as a conduit, and the dimensions of the device are approximately: length of the activated carbon section=10 cm, length of each of the particulate filters=0.64 cm, length of each of the hydrophobic filters=0.025 cm, length of each of the polytetrafluoroethylene or polypropylene connectors=4.1 cm, which yields a total length of the device of 19.7 cm.

Additionally, this embodiment used a non-additive, non-impregnated, granulated (nominal particle diameter of 2.5 mm or greater), activated carbon medium that is packed into the conduit at a density in the range of 0.7-1.2 $gm/cm^3$, and with a preferred density of approximately 1.0 $gm/cm^3$ to allow the released calibration gas to flow freely through the device at the desired flowrate of approximately 0.4-0.5 L/min. Various types of hydrating particulate or fiber filters can be used, the simplest example of which is just a cotton ball that has a density of approximately 0.5 $g/cm^3$ and has been dipped into distilled water. Preferred degrees of saturation of the particulate filter are in the range of 0.25-1.0.

The hydrophobic filter for this embodiment has been fabricated from polytetrafluoroethylene, PTFE, in order to provide it with its desired water repelling properties.

Depending upon the flowrate of the toxic gas that is to travel through the present invention and a desire to keep its dimensions small so that it is easily portable, it may be necessary to increase the density of the activated carbon bed to the point that a downstream suction device is needed in order to help draw the released toxic gas through the device. Additionally, instrumentation can be provided at various points on the device to monitor the hydrogen sulfide adsorption efficiency of the activated carbon bed and to ultimately provide an output signal which can be used to alert the device's user that it is time to discard the device, which, because of the device's method of construction, is easily disposable.

Furthermore, a source of distilled water can be provided and connected to the region of said device containing said hydrated, particulate filters so as to ensure that said filters are maintained at a desired degree of saturation throughout the lifetime of the device's use.

The foregoing is considered as illustrative only of the principles of the present invention. Further, since numerous modifications and changes will readily occur to those skilled in the art, it is not desired to limit the invention to the exact construction and operation shown and described herein. Accordingly, all suitable modifications and equivalents may be resorted to, falling within the scope of the invention that is hereafter set forth in the claims to the invention.

I claim:

1. A portable device for adsorbing a hydrogen sulfide component of a calibration gas that would otherwise be released into the surrounding atmosphere during the testing of a portable gas detector in which said calibration gas flows at a specified rate through said portable gas detector, said device comprising:

an activated carbon bed having upstream and downstream ends and a configuration adapted to allow for said specified flow rate of said calibration gas from said downstream end to said upstream end of said activated carbon bed, an upstream and a downstream hydrated, particulate filter, said upstream particulate filter situated such that it is adjacent said upstream end of said activated carbon bed and said downstream particulate filter situated such that it is adjacent said downstream end of said activated carbon bed, an upstream and a downstream hydrophobic filter, said upstream hydrophobic filter situated such that it is adjacent and upstream of said upstream hydrated, particulate filter and said downstream hydrophobic filter situated such that it is adjacent and downstream of said downstream hydrated, particulate filter, wherein said hydrophobic filters and hydrophobic filters each have configuration that are adapted to maintain the humidity level in said activated carbon bed above a set level so as to ensure a desired degree of adsorption of said hydrogen sulfide at said specified flow rate of said calibration gas, and a conduit having a configuration adapted to enclose and assemble said activated carbon bed, upstream and downstream hydrated, particulate filters and upstream and downstream hydrophobic filters and direct the flow of said calibration gas through said device at said specified flow rate.

2. The portable device as recited in claim 1, wherein:
said hydrated, particulate filters having a prescribed degree of saturation in the range of 0.25-1.0.

3. The portable device as recited in claim 1, wherein:
the configurations of said activated carbon bed, hydrated, particulate filters and hydrophobic filters are further adapted to provide said device with the property of being disposable as standard trash rather than as hazardous material.

4. The portable device as recited in claim 2, wherein:
the configurations of said activated carbon bed, hydrated, particulate filters and hydrophobic filters are further adapted to provide said device with the property of being disposable as standard trash rather than as hazardous material.

5. A method of providing a portable device for adsorbing a hydrogen sulfide component of a calibration gas that would otherwise be released into the surrounding atmosphere during the testing of a portable gas detector in which said calibration gas flows at a specified rate through said portable gas detector, said method comprising the steps of:

providing an activated carbon bed having upstream and downstream ends and a configuration adapted to allow for said specified flow rate of said calibration gas from said downstream end to said upstream end of said activated carbon bed, providing an upstream and a downstream hydrated, particulate filter, said upstream particulate filter situated such that it is adjacent said upstream end of said activated carbon bed and said downstream particulate filter situated such that it is adjacent said downstream end of said activated carbon bed, providing an upstream and a downstream hydrophobic filter, said upstream hydrophobic filter situated such that it is adjacent and upstream of said upstream hydrated, particulate filter and said downstream hydrophobic filter situated such that it is adjacent and downstream of said downstream hydrated, particulate filter, wherein said hydrophobic filters and hydrophobic filters each have configuration that are adapted to maintain the humidity level in said activated carbon bed above a set level so as to ensure a desired degree of adsorption of said hydrogen sulfide at said specified flow rate of said calibration gas, and providing a conduit having a configuration adapted to enclose and assemble said activated carbon bed, upstream and downstream hydrated, particulate filters and upstream and downstream hydrophobic filters and direct the flow of said calibration gas through said device at said specified flow rate.

6. The method as recited in claim 5, wherein:
said hydrated, particulate filters having a prescribed degree of saturation in the range of 0.25-1.0.

7. The method as recited in claim 5, wherein:
the configurations of said activated carbon bed, hydrated, particulate filters and hydrophobic filters are further adapted to provide said device with the property of being disposable as standard trash rather than as hazardous material.

8. The method as recited in claim 6, wherein:
the configurations of said activated carbon bed, hydrated, particulate filters and hydrophobic filters are further adapted to provide said device with the property of being disposable as standard trash rather than as hazardous material.

* * * * *